(12) United States Patent
Kammer et al.

(10) Patent No.: US 9,561,895 B1
(45) Date of Patent: Feb. 7, 2017

(54) USE OF STERILE SLEEVE IN PRODUCTION OF SURGICAL SLUSH

(71) Applicant: C° Change Surgical LLC, Winston-Salem, NC (US)

(72) Inventors: Patrick Kammer, Greensboro, NC (US); Kevin Joseph Rackers, Summerfield, NC (US); Philip Morrison Allred, III, Kernersville, NC (US)

(73) Assignee: C° Change Surgical LLC, Winston-Salem, NC (US)

( * ) Notice: Subject to any disclaimer, the term of this patent is extended or adjusted under 35 U.S.C. 154(b) by 0 days.

(21) Appl. No.: 15/293,612

(22) Filed: Oct. 14, 2016

Related U.S. Application Data

(63) Continuation of application No. PCT/US2016/055524, filed on Oct. 5, 2016, and a continuation-in-part of application No. 14/875,589, filed on Oct. 5, 2015.

(60) Provisional application No. 62/237,525, filed on Oct. 5, 2015, provisional application No. 62/085,590, filed on Nov. 30, 2014.

(51) Int. Cl.
  *A61F 7/00* (2006.01)
  *F25C 1/20* (2006.01)
  *B65D 85/10* (2006.01)
(52) U.S. Cl.
  CPC ........ *B65D 85/1054* (2013.01); *A61L 2202/23* (2013.01); *F25C 2301/002* (2013.01); *F25C 2400/12* (2013.01)
(58) Field of Classification Search
  CPC ....... A61M 1/0001; A61L 12/086; A61J 1/14; A61J 1/16; B65D 3/22; B65D 5/62; B65D 81/3876; B65D 85/1054; F25C 1/20; F25C 1/22; F25C 2301/022; F25C 2400/12
  USPC ................. 220/23.83, 23.86, 23.887, 23.89
  See application file for complete search history.

(56) References Cited

U.S. PATENT DOCUMENTS

| | | | | |
|---|---|---|---|---|
| 3,882,315 A | * | 5/1975 | Soldan | G21F 5/005 206/204 |
| 7,874,167 B2 | | 1/2011 | Kammer | |
| 7,950,540 B2 | * | 5/2011 | Bara | B65D 23/0885 215/209 |
| 2003/0154989 A1 | * | 8/2003 | Faries, Jr. | A61F 7/0241 128/849 |
| 2009/0301107 A1 | * | 12/2009 | Kammer | A61F 7/0085 62/68 |
| 2015/0076363 A1 | * | 3/2015 | Wen | A61L 2/10 250/455.11 |
| 2016/0151200 A1 | | 6/2016 | Kammer | |

OTHER PUBLICATIONS

Product Insert: 0.9% Sodium Chloride Irrigation, USP Baxter Sterile Container System, Jul. 2012, 7 pages, Baxter Healthcare Corporation, Deerfield, Illinois, USA.

* cited by examiner

*Primary Examiner* — Ryan J Walters
*Assistant Examiner* — Erik Mendoza-Wilkenfe
(74) *Attorney, Agent, or Firm* — Kevin E Flynn; Flynn IP Law

(57) ABSTRACT

Production of sterile therapeutic medium such as sterile surgical slush for use in surgery. A sterile slush container with a sterile sleeve assembly so that the outside of the sterile slush container remains sterile after placement in a non-sterile slush making machine so that the sterile slush container may be returned to the sterile field after removal of the sterile slush container from the sleeve assembly.

13 Claims, 19 Drawing Sheets

| 2004 | Slush bottle and lid provided to sterile field. |
|---|---|
| 2008 | Container sleeve and sleeve top are provided to sterile field. |
| 2012 | Slush bottle partially filled with sterile saline. |
| 2016 | Lid applied to slush container. |
| 2020 | Slush bottle placed into container sleeve. |
| 2024 | Sleeve top placed over lid and engages container sleeve. |
| 2028 | Sleeve assembly placed in slush making machine. |
| 2032 | Surgical slush formed in slush container. |
| 2036 | Optional Step—Hold surgical slush in slush making machine set to maintain mode. |
| 2040 | Sleeve assembly brought to edge of sterile field. |
| 2044 | Sleeve top removed outside sterile field. |
| 2048 | Scrubbed staff member takes sterile slush container from non-sterile container sleeve held outside of sterile field. |
| 2052 | Slush container is in sterile field and surgical slush may be used when needed. |

| 3004 | Flexible slush container with sterile saline placed within sterile container sleeve. |
|---|---|
| 3008 | A sleeve top engages the open end of the container sleeve. |
| 3012 | Sleeve assembly placed in slush making machine. |
| 3016 | Surgical slush formed in slush container. |
| 3020 | Optional Step—Hold surgical slush in slush making machine set to maintain mode. |
| 3024 | Sleeve assembly brought to edge of sterile field |
| 3028 | Sleeve top removed outside sterile field. |
| 3032 | Scrubbed staff member takes sterile slush container from non-sterile container sleeve held outside of sterile field. |
| 3036 | Slush container is in sterile field and surgical slush may be used when needed. |

USE OF STERILE SLEEVE IN PRODUCTION OF SURGICAL SLUSH

This application is a continuation of co-pending and commonly assigned PCT Application No. PCT/US16/55524 filed Oct. 5, 2016 for Use of Sterile Sleeve in Production of Surgical Slush. The '524 application is incorporated by reference. Through the '524 application, this application claims the benefit of and incorporates by reference U.S. Provisional Patent Application No. 62/237,525 filed Oct. 5, 2015 for Use of Sterile Sleeve in Production of Surgical Slush.

This application claims priority to and incorporates by reference co-pending U.S. patent application Ser. No. 14/875,589 filed Oct. 5, 2015 for Production of Well-Mixed Slush.

Through the '589 application, this application claims benefit of and incorporates by reference U.S. Provisional Application No. 62/085,590 filed Nov. 30, 2014 for Production of Well-Mixed Surgical Slush via Eccentric Oscillation.

BACKGROUND

Field of the Disclosure

This disclosure relates generally to the production of sterile therapeutic medium such as sterile surgical slush for use in surgery. More particularly, this disclosure is related to covering a sterile slush container with a sterile sleeve assembly so that the outside of the sterile slush container remains sterile after placement in a non-sterile slush making machine so that the sterile slush container may be returned to the sterile field after removal of the sterile slush container from the sleeve assembly.

Sterile saline slush is used in a variety of surgical applications to slow organ and tissue metabolic rates thereby protecting organs from irreversible tissue damage during cardiac, neurological organ transplant, vascular, urologic and other complex surgeries. It is important that the slush has as smooth and spherical a configuration as possible to ensure atraumatic slush without sharp crystal edges that could puncture or damage tissue. The slush should have a substantially uniform consistency to maintain optimal thermodynamic cooling performance. Surgical slush is a mix of ice crystals formed while cooling saline and some amount of liquid saline that remains in liquid form.

Unless explicit to the contrary, the word "or" should be interpreted as an inclusive or rather than an exclusive or. Thus, the default meaning of or should be the same as the more awkward and/or.

This disclosure discusses the delivery of sterile surgical slush to a slush receptacle such as a basin shown in FIG. 3. The term basin is used in subsequent descriptions. There are many slush receptacles that may receive and hold surgical slush for subsequent use. Those of skill in the art will recognize that the teachings of the present disclosure for delivery of sterile surgical slush to a basin apply to other wide mouth receptacles, whether the receptacle is called a: trough, barrel, pitcher, vat, reservoir or tank, pot, pail, jar, bucket, tub, or some other term. The term slush receptacle is intended to include the term basin and all other items that may receive and hold surgical slush for subsequent use.

This disclosure discusses the placement of a sleeve around a slush container. One example of slush container is a bottle or elongated jar with a reversibly removable lid. As described below, other slush containers may be used including bags containing slush or bag/jar hybrids with a threaded cap on one end of a bag.

SUMMARY OF THE DISCLOSURE

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

One way to summarize some of the many teachings of the present disclosure is a method for production of sterile surgical slush outside of a sterile field and subsequent delivery of sterile surgical slush to the sterile field. The method may be described as:
  placing a quantity of sterile saline into a non-sterile slush making device located outside of the sterile field, the sterile saline contained in a slush container, a set of interior and exterior surfaces of the slush container starting as sterile;
  the slush container enveloped by a sleeve assembly comprising a container sleeve that covers at least a portion of the slush container and a sleeve cap engaged with the container sleeve, the sleeve assembly is initially sterile but an exterior of the sleeve assembly is deemed not sterile not later than once the sleeve assembly with slush container is placed into the slush making device;
  removing the slush container enveloped by the sleeve assembly from the slush making device after conversion of the sterile saline to sterile surgical slush;
  separating the sleeve cap from the container sleeve to expose a portion of the slush container; and
  maintaining the slush container as sterile while removing the slush container from the container sleeve and moving the slush container into the sterile field so that the slush container may be opened and the sterile saline slush may be used when needed.

Another way to summarize some of the many teachings of the present disclosure is a sleeve assembly with a container sleeve and a sleeve cap which may be engaged with the container sleeve to envelope a slush container. The container sleeve having a set of at least one vent which allows air to move from a top end of the container sleeve to a space between a bottom of an inserted slush container and a bottom of the container sleeve to facilitate removal of the slush container from the container sleeve. The sleeve assembly including an attachment system to allow the sleeve cap to be engaged with the container sleeve and then become disengaged so that the slush container may be removed from the container sleeve.

The sleeve cap may be engaged with the container sleeve with a single-use attachment system that destroys a portion of the single-use attachment system when the sleeve cap is disengaged from the container sleeve. The portion destroyed may be on the sleeve cap or on the container sleeve.

Yet another way to summarize some of the many teachings of the present disclosure is a kit for use in production and delivery of sterile surgical slush. The kit having:

a slush container for containing sterile saline;

a container sleeve with a bottom, an open top end, and a sleeve wall between the bottom and the open top end, the container sleeve sized to receive the slush container so that a bottom of the slush container makes contact with the container sleeve bottom;

a sleeve cap which is sized to fit over a portion of the slush container extending out of the open top end of the container sleeve, and a single-use attachment system to join the container sleeve and the sleeve cap so that the slush container may be enveloped by the container sleeve and sleeve cap, and subsequent separation of the container sleeve and sleeve cap to expose the slush container extending out the open top end of the container sleeve destroys a portion of the single-use attachment system so that the container sleeve and sleeve cap are not joined together a second time.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 5 shows is a process 2000 for production of sterile surgical slush and delivery of the sterile surgical slush to a basin within a sterile field.

FIG. 25 shows a process 3000 for production of sterile surgical slush and delivery of the sterile surgical slush to a basin within a sterile field using a slush container that is a flexible container.

DETAILED DESCRIPTION

Figure 1:
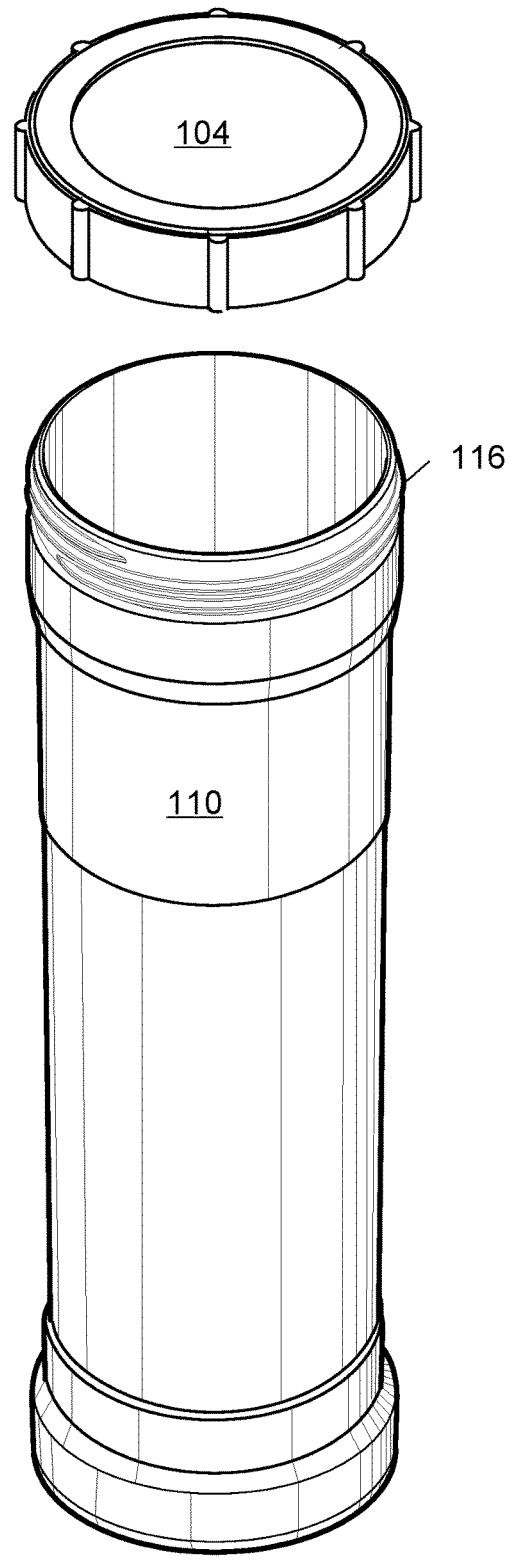
FIG. 1 shows a slush container 100 with a slush bottle 110 and a lid 104.
Figure 2:
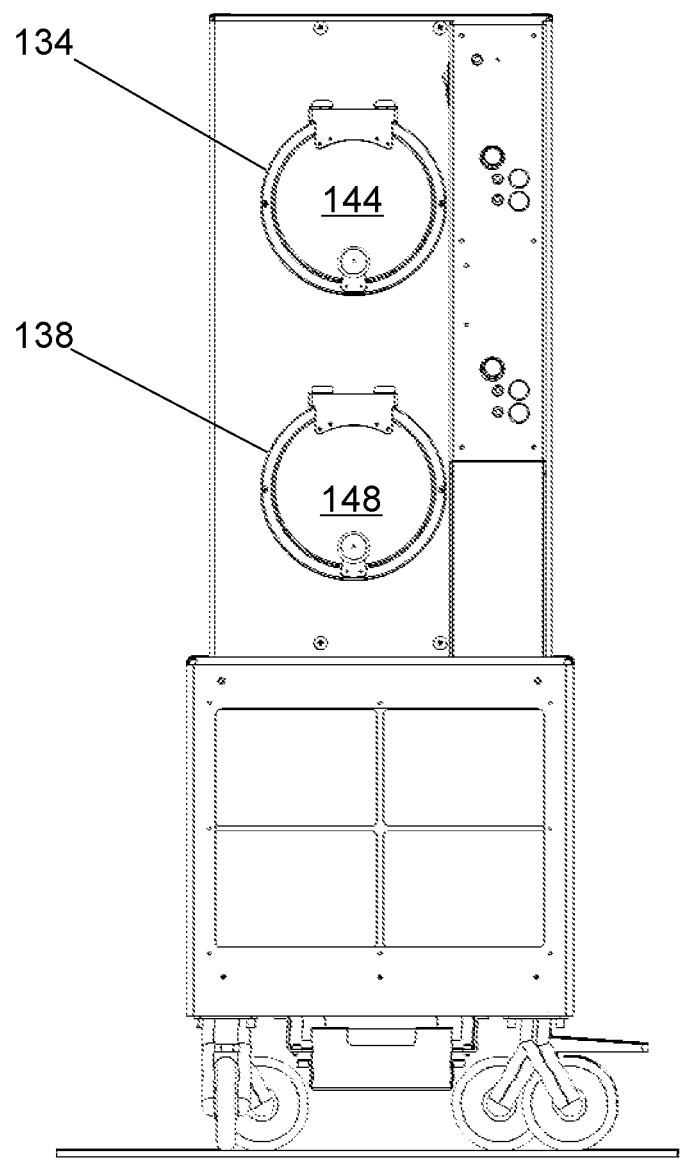
FIG. 2 shows a front plan view of a slush making machine 130.
Figure 3:
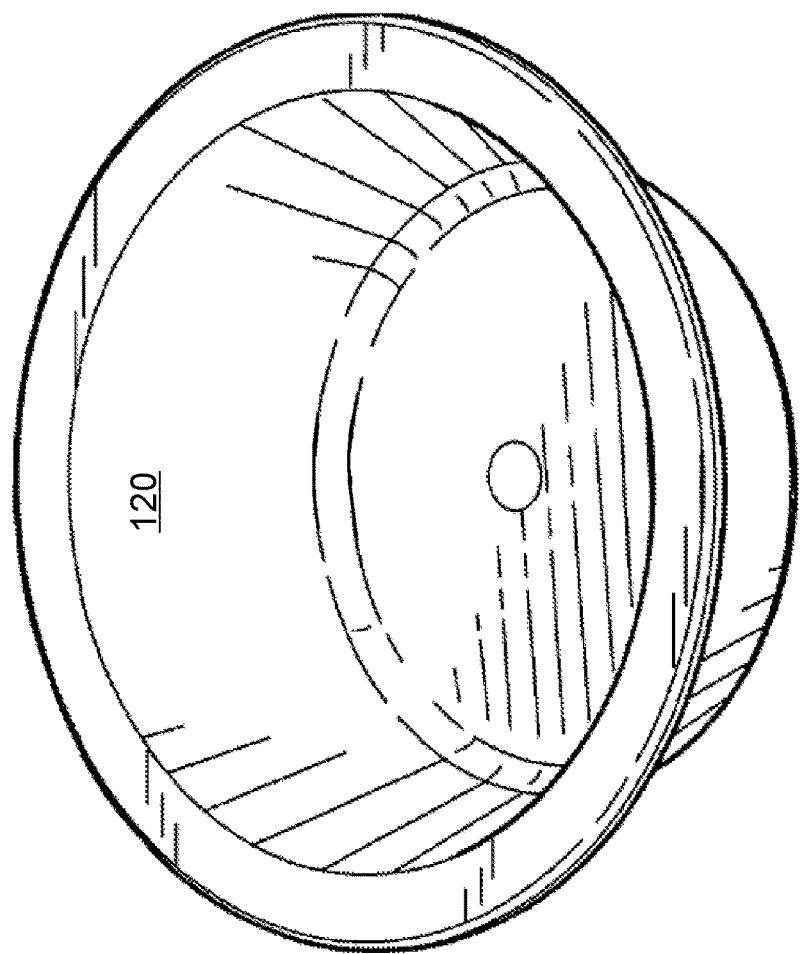
FIG. 3 shows a basin that may be placed in a sterile field and receive the surgical slush.

FIG. 1 through FIG. 3 illustrate the problem to be solved. FIG. 1 shows a slush container 100 with a slush bottle 110 and a lid 104. The lid 104 may be reversibly engaged with a set of threads 116 on the lid end of the slush bottle 110. A sterile slush bottle may be at least partially filled with sterile saline and a sterile lid 104 may be engaged. The sterile slush container 100 with contents of sterile saline and air may be then subject to chilling and agitation within a slush making machine.

FIG. 2 shows a front plan view of a slush making machine 130. The slush making machine 130 may have one or more cooling compartments. The slush making machine 130 of FIG. 2 has two cooling compartments 134 and 138. This slush making machine 130 has at least one refrigeration unit (not shown here) to cool ambient air circulated around the interiors of the cooling compartments 134 and 138. The ambient air in the first cooling compartment 134 may be isolated from the ambient air in the second cooling compartment 138 so that one cooling chamber may be operated at a different temperature from the other cooling chamber. For example, one cooling chamber may be actively cooled for the production of slush while the other cooling chamber is either not in use or is being used to maintain slush that has been created but has not been removed for use.

Each cooling compartment 134, 138 may have an access door 144 or 148. The access door 144 or 148 may be transparent to allow viewing of the activities within the cooling compartment 134 or 138 without opening the access door 144 or 148.

A slush container 100 filled with sterile saline may be placed in a slush making machine 130. For purposes of this disclosure, it does not matter how the slush making machine 130 operates beyond the fact that the slush making machine 130 creates slush within a slush container 100.

The slush making machine 130 is not considered sterile, thus after the slush container 100 is placed in the slush making machine 130, the outside of the slush container 100 even if previously sterile is now non-sterile. Thus, once the sterile saline in the slush container 100 has been converted into sterile saline slush in the slush making machine 130, it is necessary to transfer the sterile saline slush to a basin 120 (See. FIG. 3) or other suitable reservoir on a surface within the sterile field.

The concept of maintaining a sterile field to protect a surgical patient from potential pathogens is an important part of running an operating room. We need not cover all the nuances here. These points should be sufficient to introduce the relevant issues.

Not everyone in the operating room is part of the sterile field. There are people that perform necessary duties outside the sterile field but within the operating room such as the OR Circulating Nurse ("Circulator") and other non-sterile personnel. The scrubbed personnel that are in the sterile field are not allowed to touch non-sterile items as that would make the scrubbed personnel no longer sterile.

Extreme care must be taken to avoid splashing or spillage of sterile fluids.

Thus, there is a challenge to move the sterile saline slush from the slush container 100 after conversion into sterile saline slush in the slush making machine 130 and transfer the sterile saline slush into a basin 120 within the sterile field given that the non-sterile assistant holding the non-sterile exterior of the slush container 100 containing sterile slush cannot enter the area above the sterile field and the non-sterile assistant cannot hand the slush container 100 of sterile slush to a scrubbed member of the team to carry slush container 100 into the sterile field. A further complication is the desire to minimize splashing and spillage of the sterile surgical slush.

U.S. Provisional Application No. 62/085,590 filed Nov. 30, 2014 for Production of Well-Mixed Surgical Slush via Eccentric Oscillation (referenced above) includes a process for creating surgical slush in a slush making machine located outside of the sterile field and then transferring the sterile slush back into the sterile field. It is instructive for appreciating this disclosure to review that process.

Figure 4:
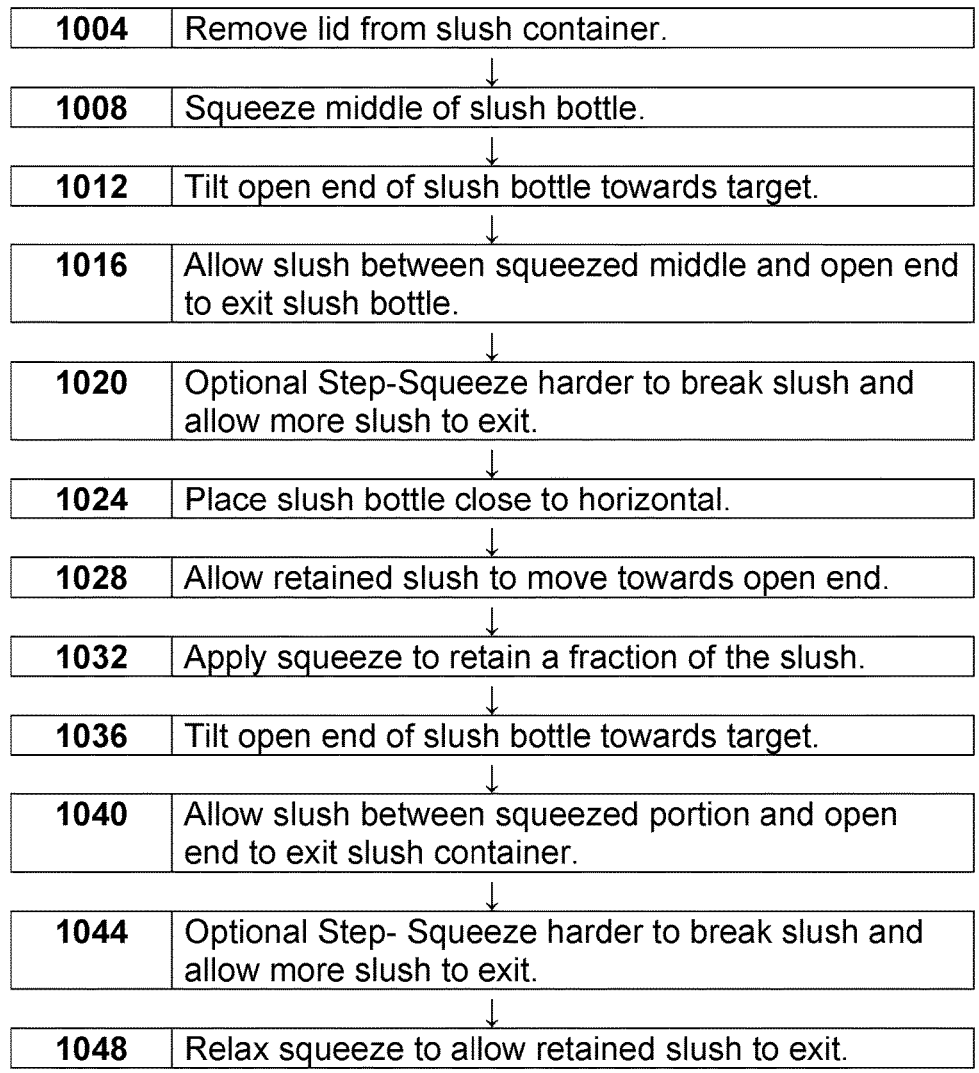
FIG. 4 provides a high-level overview of a process 1000 to deliver surgical slush into a sterile field.

FIG. 4 provides a high-level overview of a process 1000 to deliver surgical slush into a sterile field. Passing surgical slush into a basin 120 in the sterile field may be a challenging task. Unlike pouring a fluid which can be moderated by the tilt angle of the open container, pouring the semi-solid slush slurry out of an open mouth container can be a binary event where nothing comes out until the entirety of a clump of slush slurry comes out. The release of a large mass of slush can cause splashing or spillage of sterile materials from the target basin in the sterile field.

Step 1004—Remove the lid 104 from the closed slush container 100 after removal of the slush container 100 from the cooling compartment 134 of the slush making machine 130. Keep the slush container substantially upright so that slush material does not leave the open end of the slush bottle after the lid is removed from the slush container.

Step 1008—Squeezing the middle of the open slush bottle. Squeezing the middle of the open slush bottle 110 allows a user to reduce the cross sectional area of the open slush bottle to prevent a rapid slide of all contents out the open mouth of the slush bottle.

Step 1012—Tilt the open slush bottle 110 to direct the open end of the slush bottle 110 towards the target basin 120.

Step 1016—Allow some slush located between the squeezed middle and the open top to leave the slush bottle 110. As the open end of the slush bottle 110 is lowered to release slush, some slush will break away from the mass of slush as the mass of slush from the squeeze point to the bottle bottom of the slush bottle is retained by the reduction in inner cross section of the middle of the slush bottle from the squeeze.

Further tilting of the open end of the slush bottle downward may cause additional slush to release from the retained mass. Having a slush container 100 that is sufficiently translucent to allow the clump of surgical slush to be seen through the slush bottle walls is helpful with this process.

Step 1020—Optional step—Increase squeeze on the slush bottle to cause some slush to break off and leave the slush bottle.

Step 1024—Place open slush bottle 110 close to horizontal.

Step 1028—Allow retained slush to move towards open end of slush bottle 110. Slowly reducing the amount of squeeze while the open end of the slush bottle 110 is only slightly below horizontal will allow the mass of slush to move slowly towards the open end of the slush bottle 110.

Step 1032—Squeeze to retain a fraction of the slush still in the open slush bottle 110. Increasing the amount of squeeze will now retain a fraction of the slush mass as the distal end of the slush mass has moved from the bottle bottom of the slush bottle 110 but is still precluded from leaving the open slush bottle 110.

Step 1036—Tilt open end of slush bottle 110 towards target basin 120.

Step 1040—Allow slush between squeezed portion and open end to break off and leave the mass of slush retained by the squeeze.

Step 1044—Optional step—Increase squeeze on the slush bottle to cause some slush to break off and leave the slush bottle and enter the target basin while some slush is retained between the squeeze and the bottle bottom of the slush bottle.

Step 1048—Slowly removing the squeeze will allow the slush bottle to return to the original shape and release the remaining slush.

The delivery of slush to the sterile field may be modified by adding steps which initially provide a squeeze towards the lid end of the middle for an initial delivery of slush followed by one or more subsequent deliveries from setting the slush bottle in a substantially vertical orientation, releasing the squeeze and then imposing a squeeze closer to the bottle bottom of the slush bottle before tiling the slush bottle to deliver more slush.

While the process set forth above, is one viable way to deliver sterile surgical slush from a non-sterile bottle back to a sterile field, some hospitals may prefer another method.

FIG. 5 shows is a process 2000 for production of sterile surgical slush and delivery of the sterile surgical slush to a basin within a sterile field.

Step 2004—A slush container with a slush bottle and lid is provided to the sterile field. Both items are sterile.

Step 2008—A container sleeve and sleeve top are provided to the sterile field. Both items are sterile Step 2012—Sterile saline is poured into the slush bottle to partially fill the slush bottle.

Step 2016—The lid is applied to the slush container. This may be achieved by engaging threads on the lid end of the slush bottle with corresponding threads inside the lid.

Step 2020—The slush bottle is placed within the container sleeve. An alternative process might place the slush bottle into the sleeve before filling and tightening the removable lid but it may be better to tighten the removable lid before placing in the sleeve to allow the slush bottle to be firmly gripped to allow the removable lid to be tightened sufficiently.

Step 2024—A sleeve top is placed over top of the lid and engages container sleeve. Now the sterile saline material is contained within a sterile slush container which is totally enveloped by a sterile sleeve assembly comprising a container sleeve and a sleeve top.

Step 2028—The sleeve assembly is passed out of the sterile field and placed within a slush making machine. The outside of the sleeve assembly is no longer sterile.

Note—the exterior of the sleeve assembly may be first deemed non-sterile when the sleeve assembly is placed into the slush making machine or may be deemed non-sterile before then. The exterior of the sleeve assembly could be deemed non-sterile even before the slush container is placed within the sleeve assembly as long as the interior of the sleeve assembly remains sterile.

Step 2032—After a period of time, the sterile saline is converted into sterile surgical slush. At least a portion of the sleeve or sleeve top is sufficiently translucent to allow the slush formed within the closed container to be viewed. Alternatively, the process can work without observation through the sleeve or sleeve top and simply rely on the slush making cycle being sufficiently long to create slush.

Step 2036—Optional step—The sleeve assembly with sterile slush container and sterile surgical slush may be held within the slush making machine at a maintain mode to maintain the sterile surgical slush until needed.

Step 2040—The sleeve assembly with the sterile slush container and the sterile surgical slush is removed from the slush making machine and brought to the edge of the sterile field.

Step 2044—The sleeve top is removed by someone out of the sterile field to expose the lid end of the sterile slush container. Care is taken to avoid touching the slush container as the slush container is sterile and cannot be handled by someone outside of the sterile field. The sleeve top may be removed in a way consistent with the type of sleeve top. It is optional but advantageous to have a sleeve top that is removed by a non-reversible process such as removal of the tear tab ring discussed below or some other seal with a tamper proof indicator that that allows a prior attempt to remove the sleeve top to be noticed.

The inclusion of a clear indication that the sleeve top has not been removed from the sleeve and then put back on the sleeve is particularly useful if the sterile slush container encapsulated in the sleeve and sleeve top is removed from view of the sterile field. This may happen where a large capacity slush making machine is placed close to several operating rooms.

Step 2048—A scrubbed staff member from the sterile field takes the sterile slush container protruding from the non-sterile container sleeve without touching the non-sterile container sleeve that is held by a staff member outside of the sterile field.

Step 2052—The scrubbed staff member can open the sterile slush container immediately or later when additional sterile slush is needed. The exterior of the slush container is still sterile and thus does not pose any complications for transfer of the sterile surgical slush within the sterile field.

While the method set for in process 2000 could be implemented in a number of ways, in an effort to fulfill the enablement requirement of patent laws within the United States of America, this disclosure will go into great detail for the geometries of a slush container and sleeve assembly that would work with that slush container. Those of skill in the art would be able to translate the teachings of the present disclosure for use with other slush containers used in other slush making machines to obtain the benefits of the present disclosure. Thus, the geometries should be deemed educational rather than limiting.

Sleeve.

Figure 6:
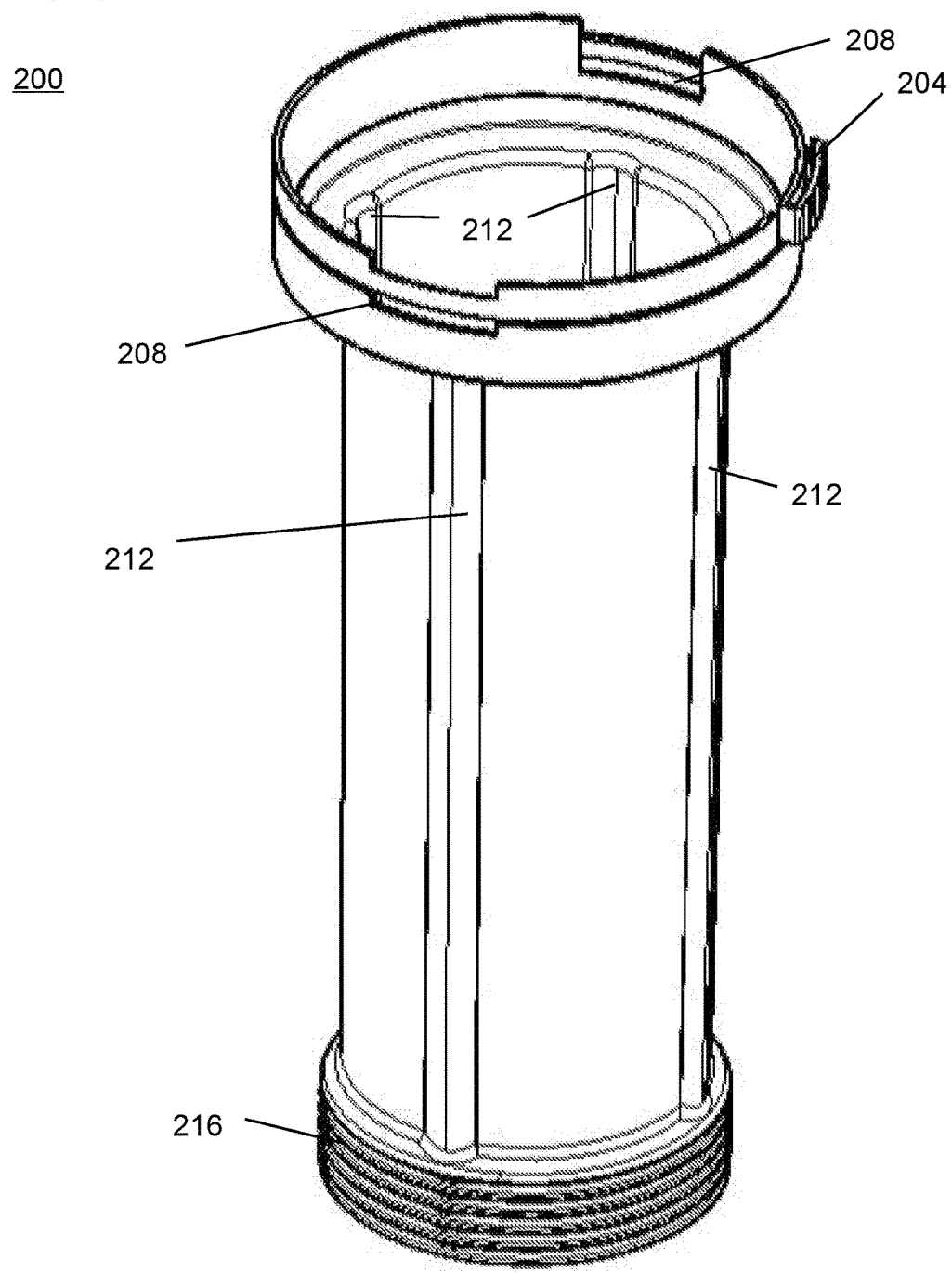
FIG. 6 shows a side perspective view of sleeve 200.

FIG. 6 shows a side perspective view of sleeve 200. Features visible include tear tab rim 204, windows 208, vents 212, and expanded bottom end 216.

Figure 7:
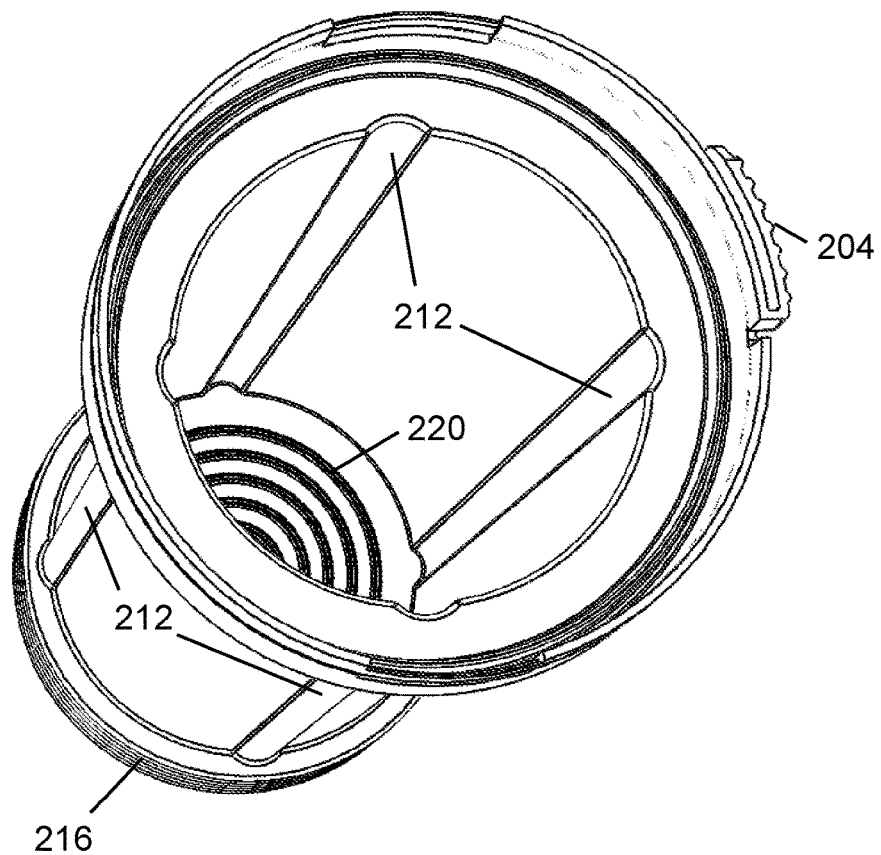
FIG. 7 shows a top perspective view of sleeve 200.

FIG. 7 shows a top perspective view of sleeve 200. Features visible include tear tab rim 204, vents 212, and expanded bottom end 216. Bottom ridges 220 maintain a small separation between the bottom of the slush bottle 440 and the bottom of the sleeve 200. The bottom ridges 220 may be helpful for allowing air to flow back into the bottom of the sleeve through the vents 212 as the slush bottle 440 is removed from the sleeve 200. To the extent that the bottom of the outside of the slush bottle 440 is not flat but had an external ring or raised area from the injection molding process, the bottom ridges 220 may be omitted.

Figure 8:
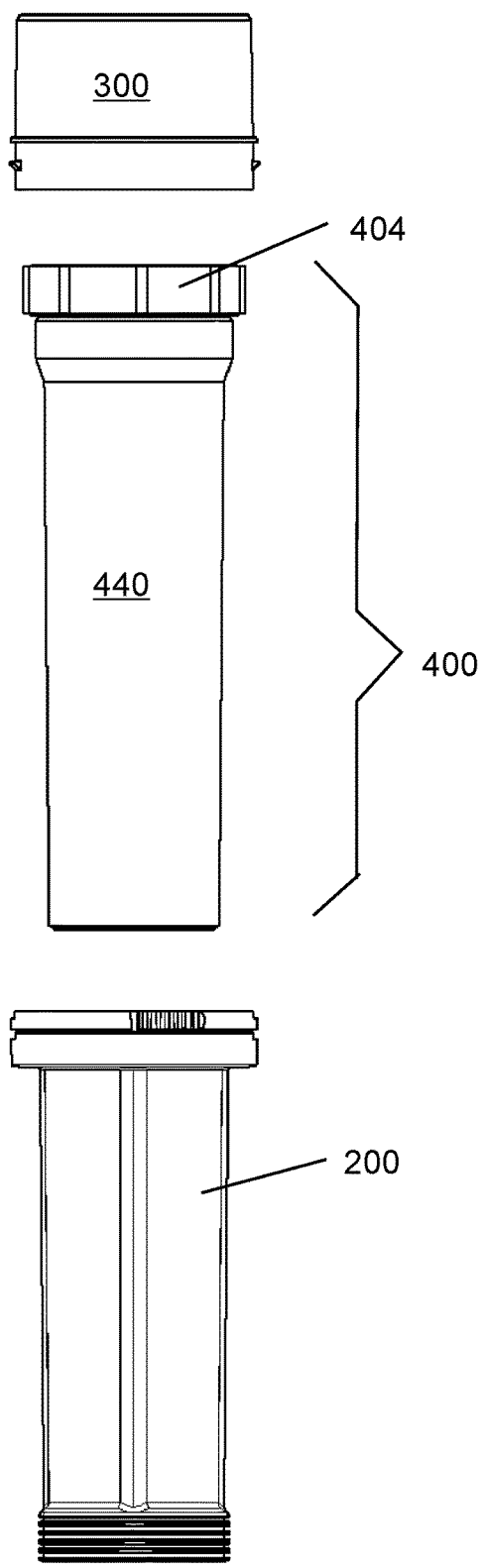
FIG. 8 shows the relationship between the sleeve 200, slush container 400, with slush bottle 440 that substantially fits within the sleeve 200, and removable lid 404 that extends beyond the sleeve 200, and sleeve cap 300 that engages with the sleeve 200 until the tear tab rim 204 is removed from the sleeve 200.

FIG. 8 shows the relationship between the sleeve 200, slush container 400, with slush bottle 440 that substantially fits within the sleeve 200, and removable lid 404 that extends beyond the sleeve 200, and sleeve cap 300 that engages with the sleeve 200 until the tear tab rim 204 is removed from the sleeve 200.

Figure 9:
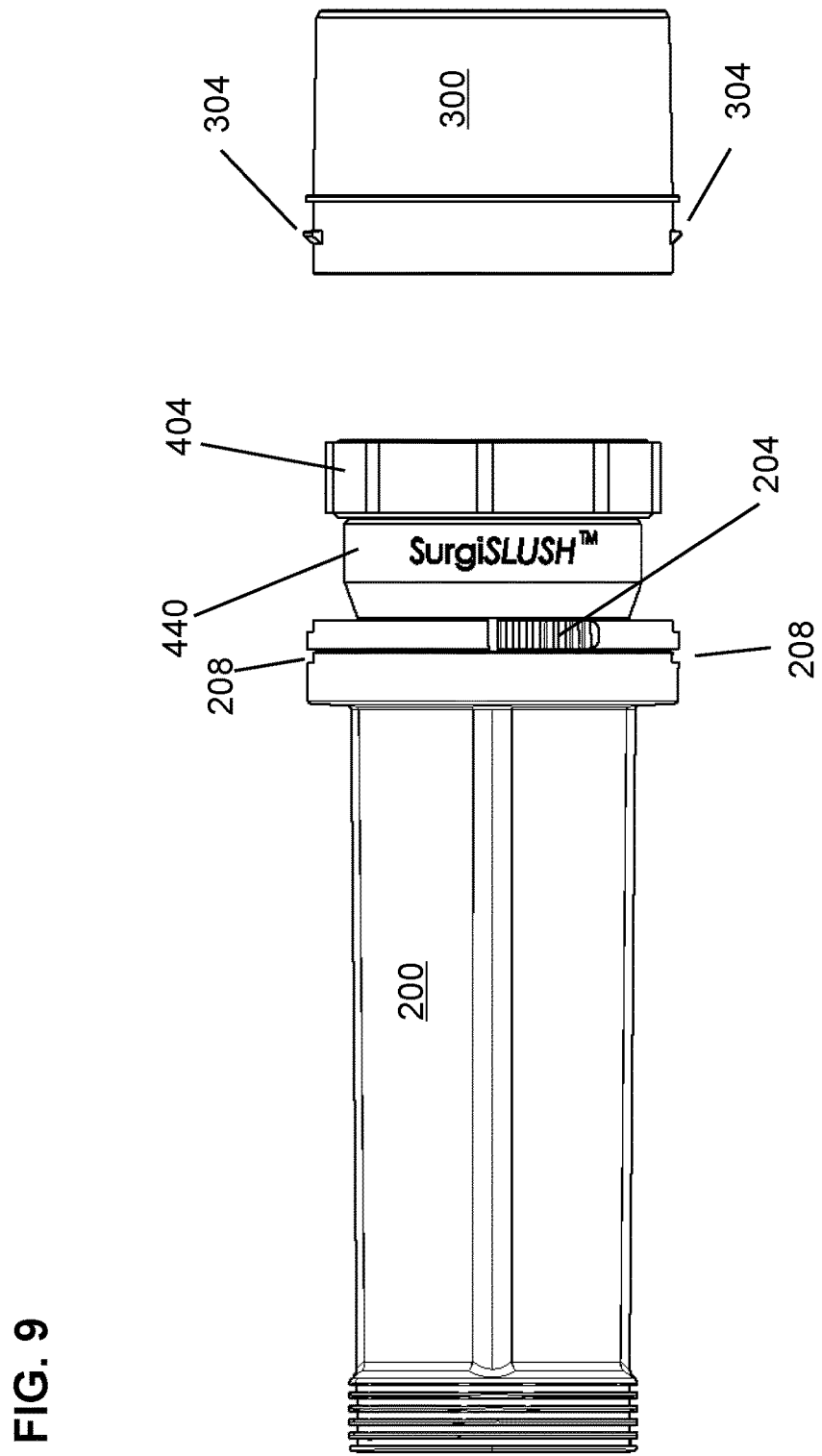
FIG. 9 shows a slush bottle 440 with engaged lid 404 inserted into sleeve 200.

FIG. 9 shows a slush bottle 440 with engaged lid 404 inserted into sleeve 200. Sleeve cap 300 fits over the portion of the slush bottle 440 and the engaged lid 404. Sleeve cap 300 has a set of at least one catch tab 304. FIG. 9 shows an embodiment with two catch tabs 304 that engage two windows 208 in the sleeve 200 until the tear tab rim 204 is removed to remove the top edge of the windows 208 and thus free the catch tabs 304.

Figure 10:
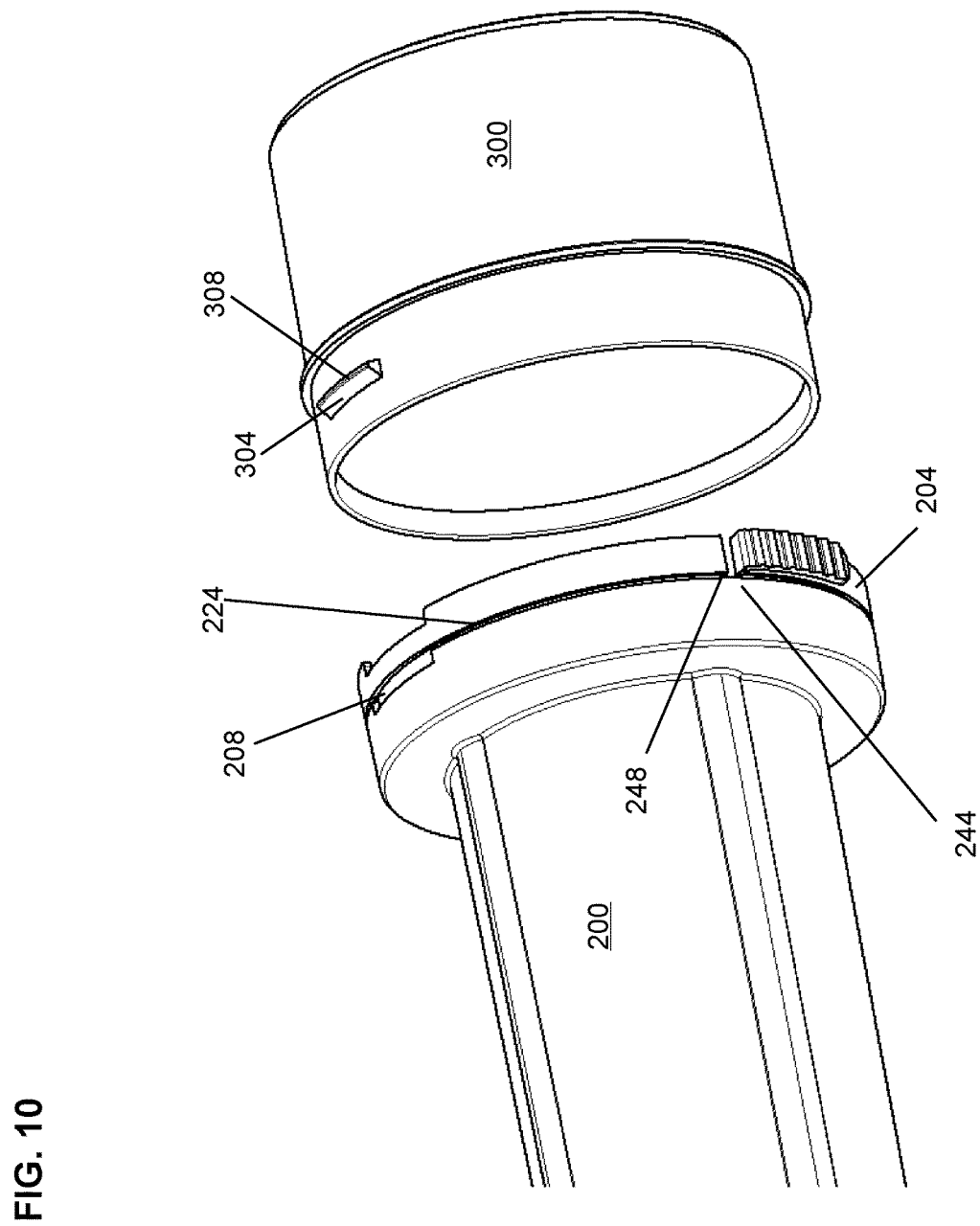
FIG. 10 shows the upper portion of the sleeve 200 and the sleeve cap 300.

FIG. 10 shows the upper portion of the sleeve 200 and the sleeve cap 300. The slush bottle 440 and lid 404 are omitted from this figure to focus attention. The catch tab 304 has an asymmetric shape so that when the sleeve cap 300 moves towards the sleeve 200, the wedge shape of the advancing catch tab 304 presses outward on the tear tab rim 204 until the catch tab 304 engages with window 208. The substantially flat face 308 of the catch tab 304 engages with the tear tab rim 204 that forms a portion of the perimeter of the window 208.

One can observe that if the tear tab rim 204 is separated from the sleeve 200 starting at start 244 and continuing to end 248, that the window 208 would no longer hold the catch tab 304 captive. Removal of the tear tab rim 204 is facilitated by a groove 224 that has less wall thickness than the adjacent surfaces to help channel the tearing action. The groove 224 runs along the lid side of the window 208.

Figure 11:
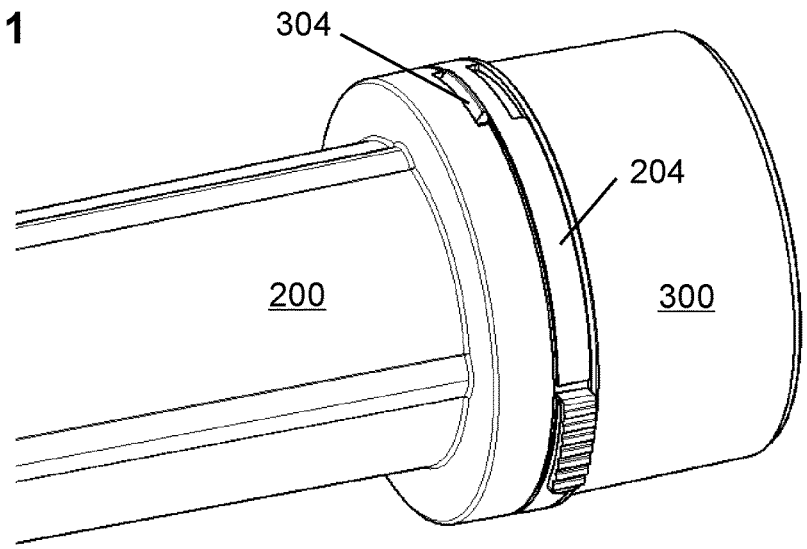
FIG. 11 shows the sleeve assembly before the removal of the tear tab rim 204.
Figure 12:
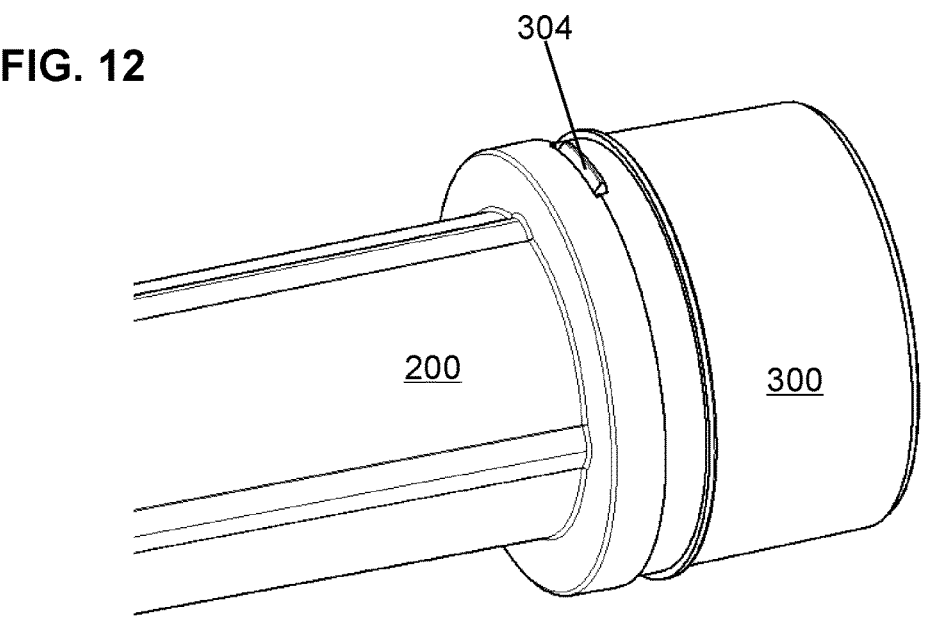
FIG. 12 shows the sleeve assembly immediately after the removal of the tear tab rim 204.

FIG. 11 and FIG. 12 show the upper end of the sleeve assembly 390 with the sleeve 200 and sleeve cap 300. FIG. 11 shows the sleeve assembly before the removal of the tear tab rim 204. FIG. 12 shows the sleeve assembly immediately after the removal of the tear tab rim 204. With the tear tab rim 204 removed, the catch tab 304 is no longer captive to the window 208 on the sleeve 200 as the tear tab rim 204 was a portion of the perimeter of the window 208.

Figure 13:
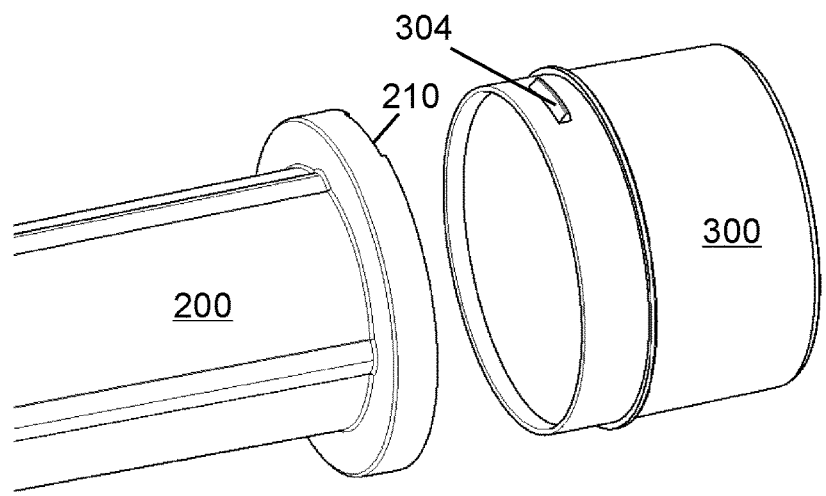
FIG. 13 illustrates that sleeve cap 300 may be removed from the sleeve 200 after removal of tear tab rim 204 as window 208 is now a ruptured window 210 which does not constrain catch tab 304.

FIG. 13 illustrates that sleeve cap 300 may be removed from the sleeve 200 after removal of tear tab rim 204 as window 208 is now a ruptured window 210 which does not constrain catch tab 304. In order to provide focus on the elements of interest, slush bottle 440 and lid 404 have been rendered invisible.

One of skill in the art will appreciate that having to remove the tear tab rim 204 in order to remove the slush sleeve cap 300 from the sleeve 200 precludes someone from accessing the slush container 400 and returning the sleeve cap 300 without leaving an unmistakable indication that someone had removed the tear tab rim 204. Thus, a tear tab rim 204 or some other sealing mechanism that must be permanently altered to allow access is desirable as it reduces the chance that a slush container 400 that had been previously accessed and may no longer be sterile be accidently used thinking that the slush container was still ensured to be sterile. One may call such a seal a tamper proof indicator.

Figure 14:
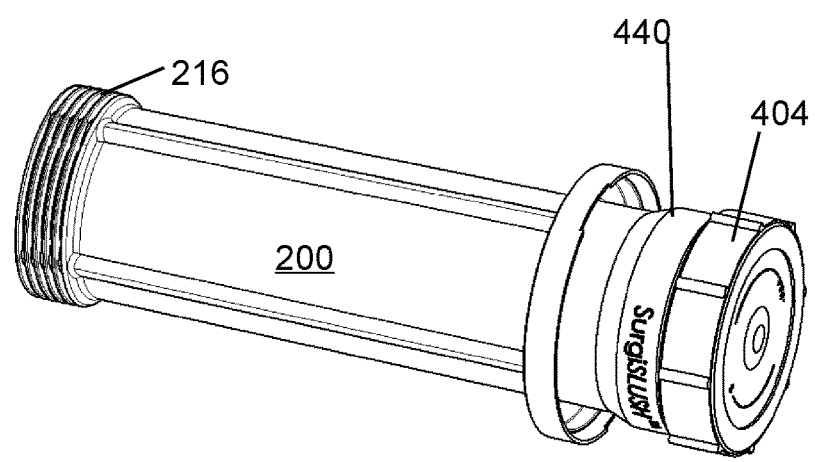
FIG. 14 shows the lid end of the slush bottle 440 and the engaged lid 404 protruding from the sleeve 200 after removal of the sleeve cap 300.

FIG. 14 shows the lid end of the slush bottle 440 and the engaged lid 404 protruding from the sleeve 200 after removal of the sleeve cap 300 (not shown here). Viewing FIG. 14, it is easy to envision a person outside the sterile field holding the sleeve 200 near the expanded bottom end 216 and maintaining the position of the sleeve 200 as someone from within the sterile field pulls the protruding but still sterile slush bottle 440 and lid 404 out the open end of the sleeve 200.

Figure 15:
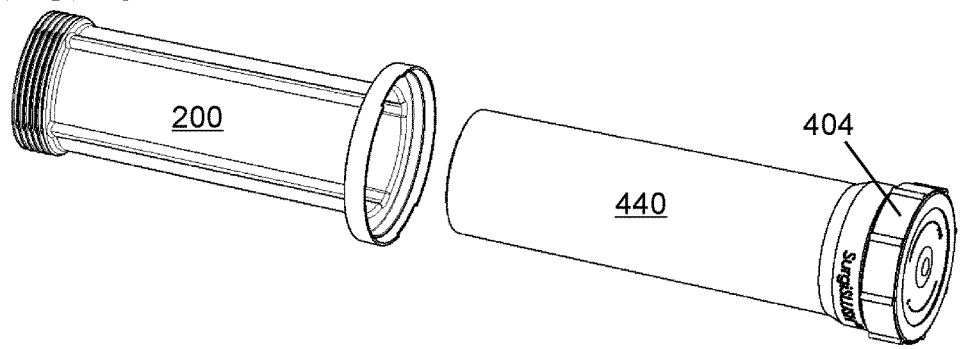
FIG. 15 shows the slush bottle 440 and lid 404 free of the sleeve 200.

FIG. 15 shows the slush bottle 440 and lid 404 free of the sleeve 200.

Vents.

The vents 212 in the sleeve 200 serve two important purposes when the outer dimensions of the slush bottle are substantially equal to the inner dimensions (excluding vents) of the sleeve 200. The vents 212 allow air to flow out of the sleeve 200 as the slush bottle 440 is inserted into the sleeve 200. Likewise the vents 212 allow air to enter into the sleeve 200 as the slush bottle 440 is being removed from the sleeve 200. This venting action reduces the forces that would otherwise need to be applied to work against a pressurized zone ahead of a slush bottle 440 during insertion or a vacuum formed below a slush bottle 440 during removal of a slush bottle 440 from a sleeve 200.

Figure 16:
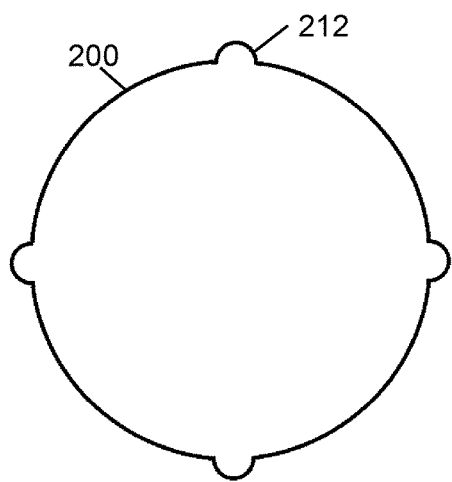
FIG. 16 shows a cross section of a sleeve 200 before insertion of a slush bottle 440.

A second function of the vents 212 is to serve as hinges to allow the inner diameter of the sleeve 200 to expand slightly when a slush bottle 440 is inserted into the sleeve 200. The hinge function is illustrated in FIG. 16 which expands as the slush bottle 440 is inserted to assume the expanded shape shown in FIG. 17. The change is shape of FIG. 17 is exaggerated here to help convey the hinge concept.

Using the ability of the vents 212 to serve as hinges and expand the diameter of the sleeve 200, the outer diameter of the slush bottle 440 can be selected to slightly exceed the inner diameter of an empty sleeve 200. Stretching the sleeve 200 a bit helps ensure contact between the thin sleeve 200 and the slush bottle 440 to avoid a layer of air that would retard heat transfer.

As both the slush bottle 440 and the sleeve 200 are created with a taper of approximately one degree to facilitate removal from the injection molding mold, the slush bottle 440 may be inserted within the sleeve 200 without a need for stretching of the hinges until about the last half inch of insertion.

Figure 17:
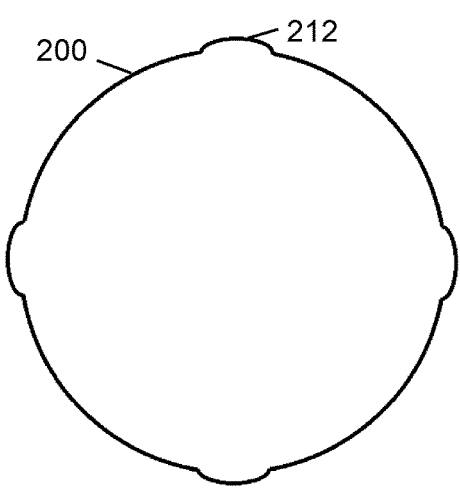
FIG. 17 shows a cross section of a sleeve 200 after insertion of a slush bottle 440.

The actual size difference of the slush bottle 440 outer diameter versus the inner diameter of the sleeve 200 may be in the range of 0.010 inches which is sufficient to promote intimate contact and effective heat transfer but not require as significant of a hinge effect as illustrated in FIG. 17.

One could use a sleeve 200 that has an inner diameter that is slightly greater than the outer diameter of the slush bottle 440 so that the hinge effect is not required. However, using a sleeve 200 that has an inner diameter that is slightly greater than the outer diameter of the slush bottle 440 leaves an air gap over the bulk of the surface of the slush bottle 440. This air gap serves as an insulator and may impede the heat transfer to more than double the required time to create slush.

The areas of the vents 212 will have reduced heat transfer as they vents 212 will have a layer of air between the vent 212 and the slush bottle 440 but this is a relatively small percentage of the surface area of the slush bottle 440.

Sleeve with Tear Tab on Sleeve Cap.

The sleeve assembly disclosed above had a tear tab rim 204 on the sleeve 200 as a single use fastener so that once the sleeve cap 300 was engaged with the sleeve 200, the tear tab rim 204 would need to be removed to release the sleeve cap 300 from the sleeve 200. Once the tear tab rim 204 was removed, the sleeve 200 would be easily recognized as a sleeve that had been used and the exterior can no longer be assumed to be sterile.

While the teachings of this disclosure favor the use of a single use fastener, the single use fastener may have the tear tab on the sleeve cap instead of the sleeve. Demonstration of this variation is shown in sleeve 1200 and sleeve cap 1300 shown in FIG. 18 to FIG. 22.

Figure 18:
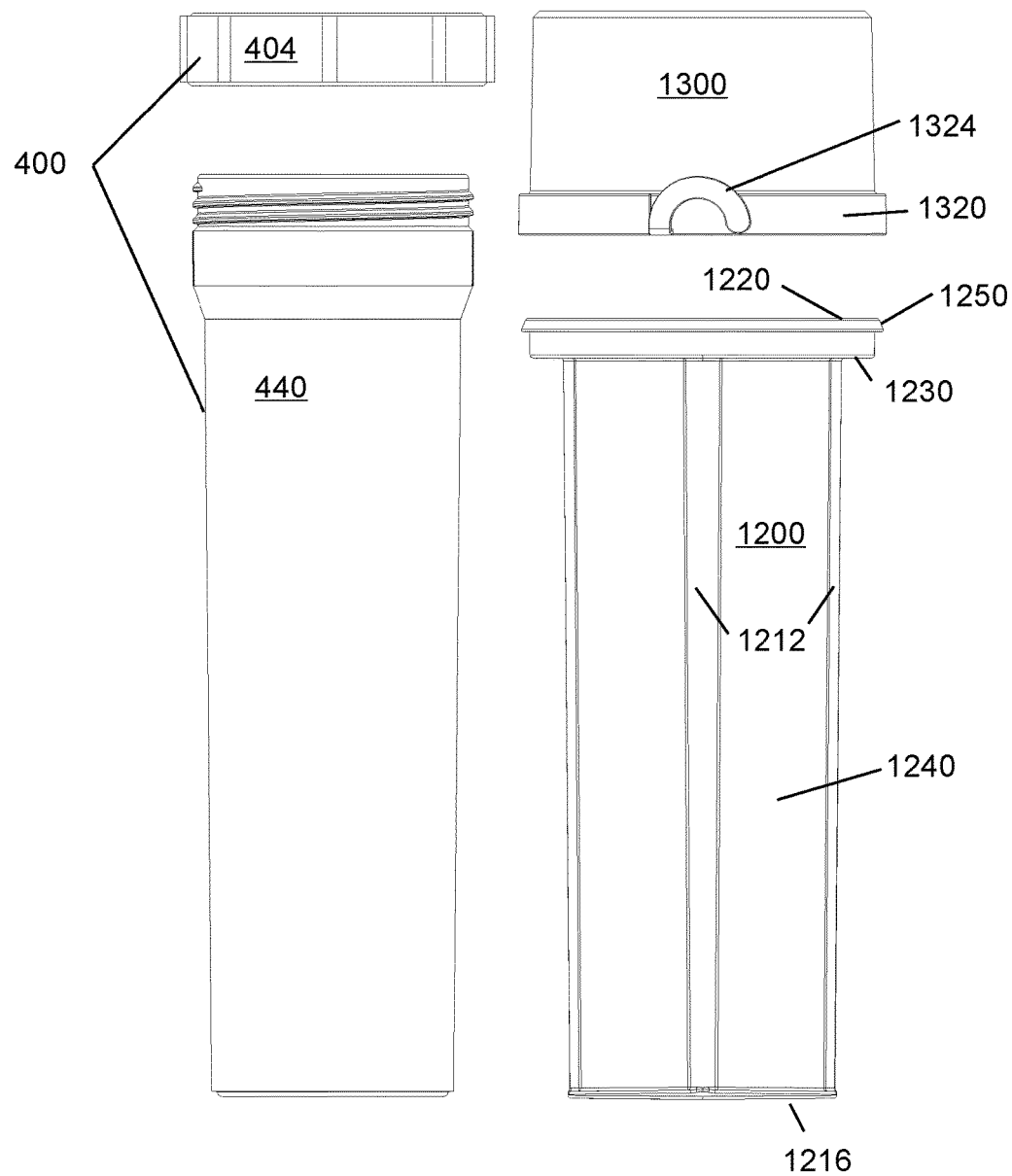
FIG. 18 shows a side view of slush bottle 440 with lid 404, as well as sleeve 1200 with sleeve cap 1300.

FIG. 18 shows a side view of slush bottle 440 with lid 404, as well as sleeve 1200 with sleeve cap 1300. Sleeve cap 1300 has tear tab rim 1320 with tear tab handle 1324. As discussed below, pulling on the tear tab handle 1324 peels off the tear tab rim 1320 to release an engaged sleeve cap 1300 from a sleeve 1200.

Sidewall 1240 runs from the bottom end 1216 to the open top 1220 of the sleeve 1200. As discussed below, the sleeve 1200 has a set of at least one vent 1212 (in this example four vents). The sleeve 1200 has an annular flange 1230 and an upper lip 1250 for engagement with the sleeve cap 1300.

Figure 19:
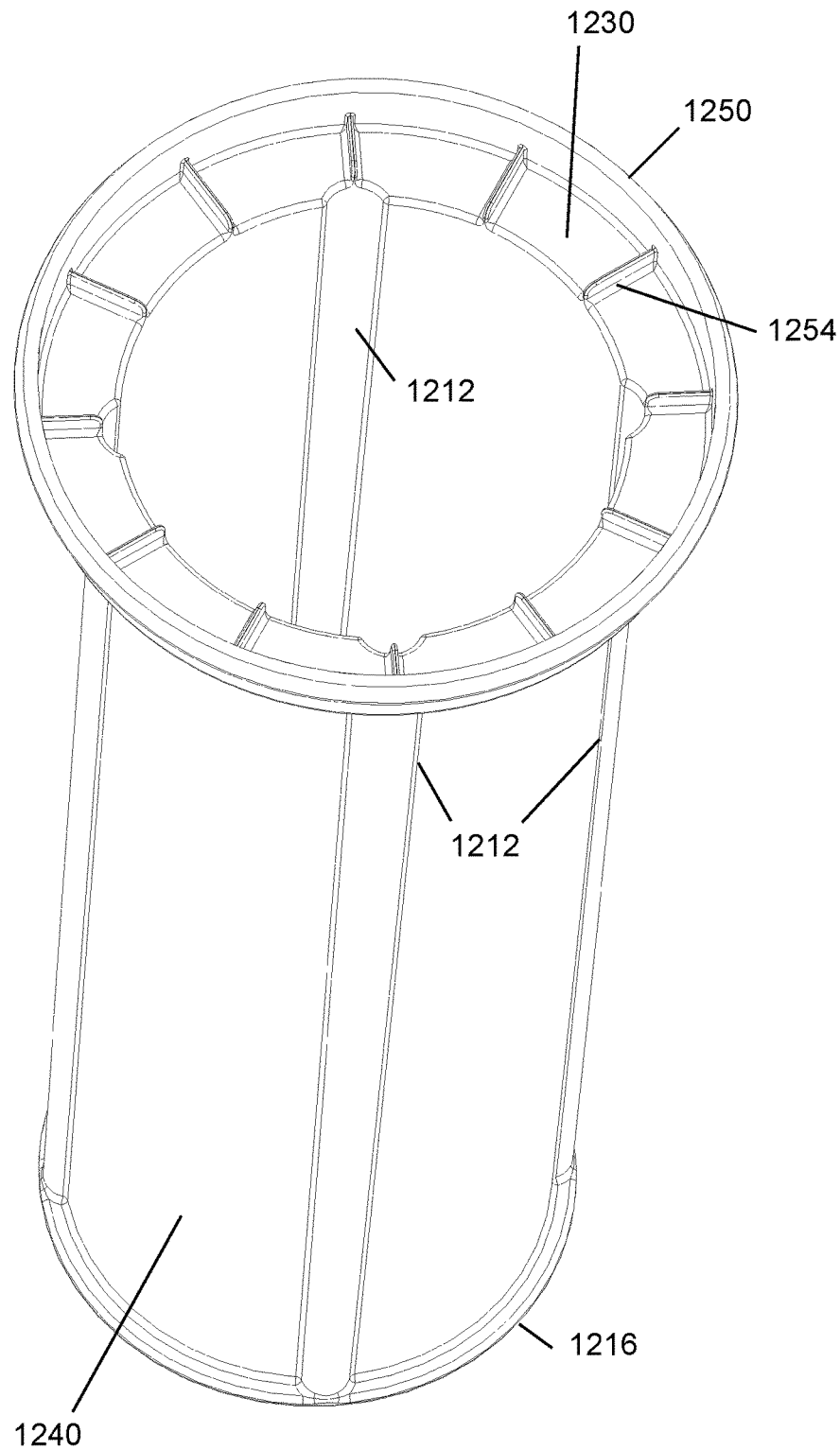
FIG. 19 show top perspective view of sleeve 1200.

FIG. 19 show top perspective view of sleeve 1200. Visible are bottom end 1216, sidewall 1240, vents 1212, the top side of annular flange 1230 and upper lip 1250. Visible in this view are optional ribs 1254 which help to stiffen annular flange 1230 so that the annular flange 1230 stays sufficiently rigid for the sleeve cap 1300 to engage the upper lip 1250. One of skill in the art may choose to alter the thickness of annular flange 1230 or make other accommodations rather than use the optional ribs 1254.

Figure 20:
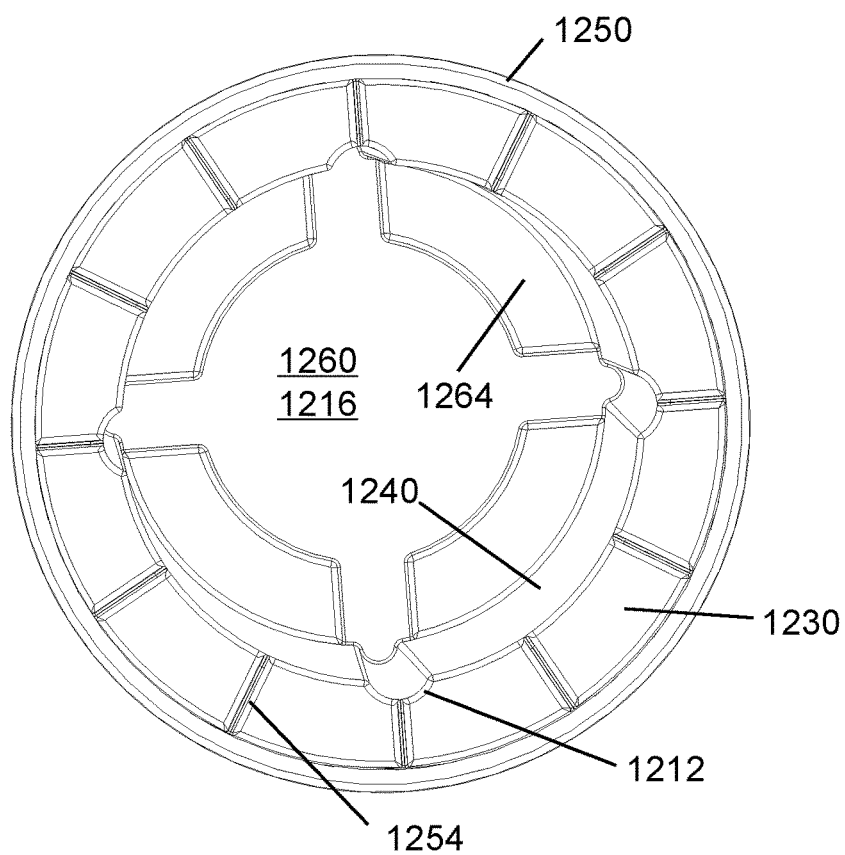
FIG. 20 shows another top perspective view of sleeve 1200 but is taken from an orientation that allows the bottom end 1216 of the interior of the sleeve 1200 to be seen.

FIG. 20 shows another top perspective view of sleeve 1200 but is taken from an orientation that allows the bottom end 1216 of the interior of the sleeve 1200 to be seen. Vents 1212 connect the air above the annular flange 1230 with a vented space 1260 at the bottom end 1216 of the interior of the sleeve 1200. The vented space 1260 is below the inserted slush container 400 as the bottom of the slush container 400 cannot go beyond the raised areas 1264. The vents 1212 and vented space 1260 allow the slush container 400 to be inserted and removed from the sleeve 1200 which is sized to be a snug fit with the slush container 100. The sleeve 1200 may be sized to slightly expand through a hinge action at the vents 1212 to have an interference fit with the lower portions of the slush bottle 440.

Figure 21:
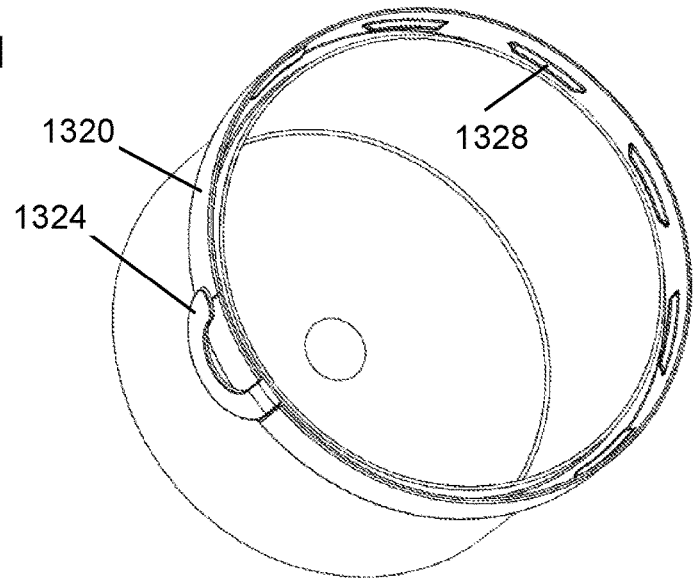
FIG. 21 is a bottom side perspective view of sleeve cap 1300.

FIG. 21 is a bottom side perspective view of sleeve cap 1300. The tear tab rim 1320 has a tear tab handle 1324 and a set of protrusions 1328. The protrusions 1328 are used to engage the upper end of the sleeve 1200. Once the set of protrusions 1328 are engaged with the upper end of the sleeve 1200, the sleeve cap 1300 is disengaged from the sleeve 1200 to expose the slush container 400 by pulling on the tear tab handle 1324 to remove the tear tab rim 1320 including the protrusions 1328 engaged with the upper end of the sleeve 1200.

Figure 22:
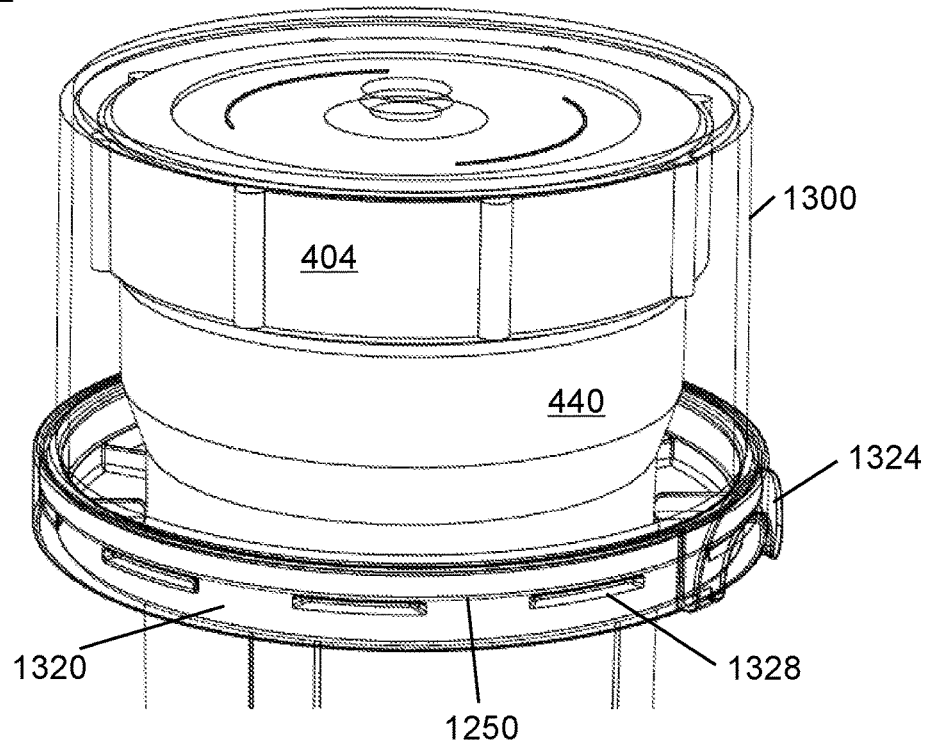
FIG. 22 is a top side perspective view of the upper portion of the sleeve assembly 1390 with a sleeve 1200 and sleeve cap 1300.

FIG. 22 is a top side perspective view of the upper portion of the sleeve assembly 1390 with a sleeve 1200 and sleeve cap 1300. The sleeve cap 1300 has been rendered transparent to show the engagement of the set of protrusions 1328 with the upper lip 1250 of the sleeve 1200. The lid 404 and slush bottle 440 are visible through the transparent sleeve cap 1300.

Pulling on the tear tab handle 1324 to remove the tear tab rim 1320 from the sleeve cap 1300 disengages the set of protrusions 1328 from the upper lip 1250 of the sleeve 1200 to disengage the sleeve cap 1300 from the sleeve 1200. Once the tear tab rim 1320 has been removed, the sleeve cap 1300 is readily identified as having been used and thus presumably no longer sterile on the exterior surface.

Means for Releasing.

The term "means for releasing" includes a tear tab on the sleeve as illustrated in connection with sleeve 200 and a tear tab on the sleeve cap 1300. These solutions may alternatively be referenced within the set of single-use attachment systems as the partial destruction of the sleeve assembly to disengage the sleeve cap from the container sleeve marks the container sleeve as unsuitable for subsequent use.

Material Choices.

The sleeve 200 may be made of a polyethylene such as Linear Low Density Polyethylene (LLDPE). The sleeve 200 may be relatively thin such as between 0.010 inches thick to 0.025 inches thick. Thin walls help heat transfer.

Sleeves may be made from other materials such as polypropylene, polyolefin, or analogous materials.

ALTERNATIVES AND VARIATIONS

Single Use Versus Mult-Use.

The teachings of the present disclosure may be used with a slush bottle 440 and lid 404 that are suitable for sterilization and reuse. Alternatively, the present disclosure may be used with single use slush containers including slush containers that are pre-filled with sterile saline and an air gap and provided with the exterior of the single use slush container sterilized.

While the use of a tear tab ring or other tamper proof indicator on the sleeve cap 1300 would render the sleeve cap 1300 a single use item, the sleeve 1200 could be made in a way that allows for sterilization and reuse. The thin wall of the sleeve 1200 and the need for a conforming fit with the slush bottle 440 may lead designers to prefer a single use sleeve 1200.

One of skill in the art will recognize that if the tear tab ring or other tamper proof indicator was placed on the top end of the sleeve 200 rather than the lower end of the sleeve cap 300, that the sleeve cap may be made in a way that allows for sterilization and reuse.

Orientation of the Slush Container within the Container Sleeve.

In some instances a slush container will have a larger end and a smaller end. One example of this is when there is a threaded lid that engages with external threads on a cylindrical container. When the slush container has a larger end, many designers may find that a suitable design places the larger end at the open top end of the container sleeve so that the sleeve top can be sized to cover this larger end.

In the event that the slush container does not have a larger end, such as when a slush bottle has a lid that engages a threaded section on the interior of a slush bottle, or when a bag is used instead of a bottle, it is possible that the end of the slush container that is opened to dispense sterile saline slush may be placed in the bottom of the container sleeve rather than the top.

Use of Other Single Use Sleeve Assemblies

While the present disclosure shows the use of a tear tab on either the sleeve or the sleeve cap to require a partial destruction of a sealed sleeve assembly 390, this is not required for all uses of the teachings of the present disclosure. Those of skill in the art will appreciate that there are a number of sealing mechanisms that allow a container to be sealed and require some destructive action in order to open the container. This sort of tamper resistant packaging is common for the peace of mind of the consumer or to reduce opportunities for theft. Sleeve assemblies may for use consistent with the teachings of the present disclosure may use any of these known sealing techniques as adapted for a sealing assembly.

Use of Other Forms of Tamper Indicators.

As noted above, both components of the sleeve assembly 390 may be configured so that unsealing the sleeve assembly 390 does not alter either component. When using a sleeve assembly with at least one component that is irreversibly altered when opened one may choose to use other tamper indicators. One known tamper indicator is to place a sticker across a sealing interface such that subsequent opening of the sealed item rips or otherwise alters the sticker. There are stickers that change appearance when placed under strain. These stickers would be altered by either the opening of the container or by efforts to remove the sticker and place the sticker back upon the container.

Figure 23:
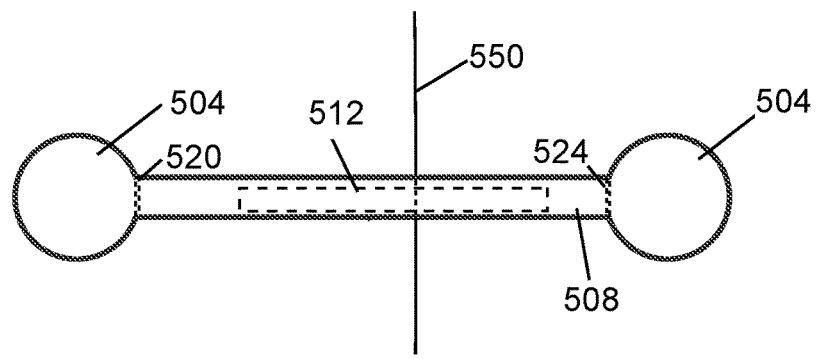
FIG. 23 shows a sticker based solution for detecting tampering.

FIG. 23 shows a sticker based solution for detecting tampering. After the sleeve cap is placed upon the sleeve, a sticker 500 is placed across a border 550 between a sleeve and a sleeve cap. The sleeve and sleeve cap may connected by a threaded connection to allow the sleeve and sleeve cap to be sterilized and reused. Other reversible connections may be used that are suitable for the conditions that the sleeve assembly will be subjected to, including the treatment of the sleeve assembly in the slush making machine. As the specifics of the reversible connection are not material to the discussion of the sticker, these details are not shown in FIG. 23.

The sticker 500 may come in this barbell shape with two enlarged adhesive areas 504 connected by a thin connector 508. The thin connector 508 may have one or more frangible sections 520 and 524. These frangible sections 520 and 524 are easily broken when the sleeve cap is removed from the container sleeve as it takes much less energy to break one of the frangible sections 520 or 524 compared with pulling one of the enlarged adhesive areas 504 from the container sleeve or sleeve cap. Note there is not a requirement that the sticker 500 be placed so that the midpoint of the sticker 500 aligns with the gap 550 separating the container sleeve from the sleeve cap.

An optional additional level of security may be added by obtaining stickers 500 that have a sequence of serial numbers written on the sticker such is in location 512. The serial number of the sticker 500 may be noted after application of the sticker 500. When the sleeve assembly 390 is brought back after the conversion of sterile saline to sterile surgical slush, the serial number may be compared with the previously recorded serial number. One vendor for a barbell sticker 500 is NovaVision (www.novavision.com) which sells a non-residue security label that is 2.875 inches by 0.5 inches in footprint and is perforated at each end of the thin connector 508.

The sticker 500 could be applied after the sleeve and sleeve cap have left the sterile field. This would avoid the need to have the stickers 500 sterilized so that they could be applied within the sterile field. Alternatively, the stickers may be sterilized and applied from within the sterile field.

No Use of Tamper Indicators.

While the use sleeve assemblies which are altered when opened or other tamper indicators may be done in accordance with the teachings of the present disclosure, the use of a sleeve assembly 390 to maintain the sterility of the outer surface of a slush container may be done without the use of tamper indicators. Tamper indicators may not be valued if the slush making machine is in secured or is in sight of the surgical team.

Sterilized and Ready for Slush Making Machine.

One of skill in the art will recognized that a slush container 400 that was prefilled with saline and an air gap and enclosed in a sleeve and sleeve cap could be delivered to the hospital sterilized and in protective wrapping. The procedure for use for would be to remove the sleeve assembly from the protective wrapping and insert into the slush making machine. The process could then continue as set forth in this disclosure to deliver the still sterile slush container to the sterile field with the surgical slush within.

Textured Surface of Sleeve.

Some or all of the container sleeve may be designed to have a texture. The texture would serve two purposes. The texture may make the sleeve easier to grasp and carry. The texture may help with heat transfer by converting the air flow within the slush making device from laminar flow to turbulent air flow or at least flow that is approaching turbulent.

Figure 24:
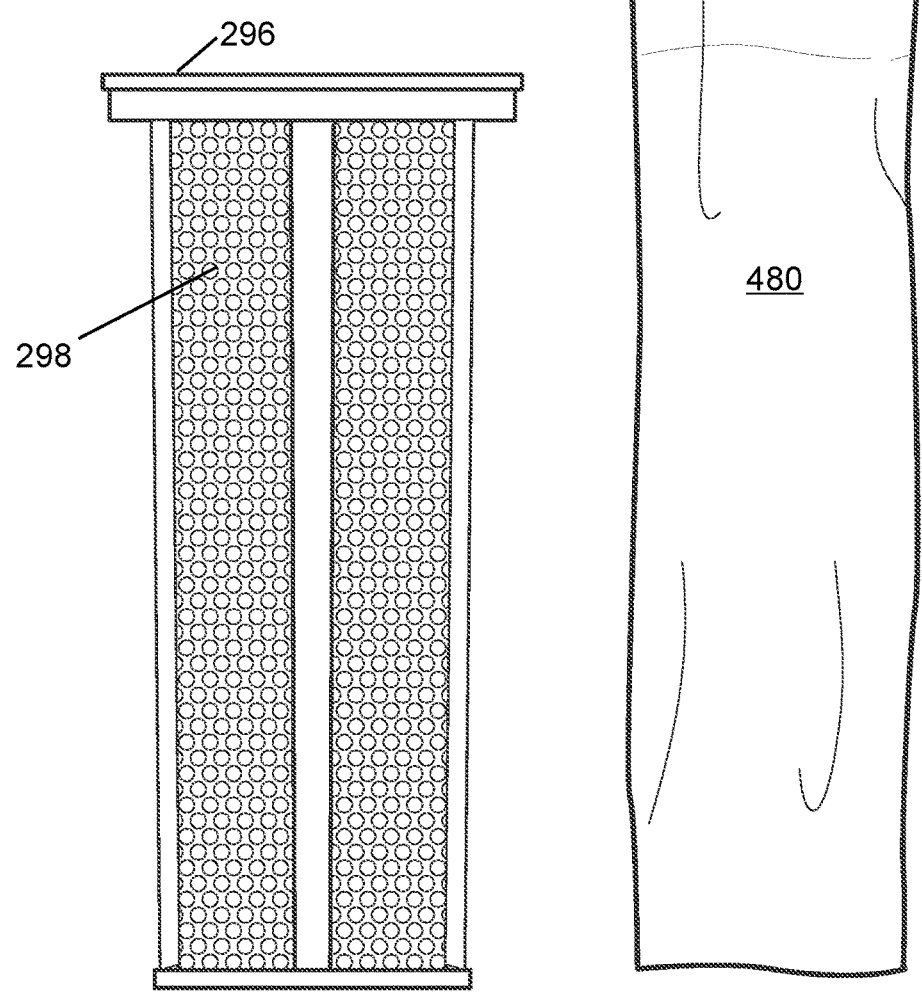
FIG. 24 includes a textured section 298 to illustrate the concept of adding texture to a sleeve.

Many different textures could be used. One suitable texture has a series of relatively flat dimples that project outward from the exterior surface of the sleeve. The height of the flat dimples may be on the order of magnitude of 0.003 to 0.004 inches. The diameter of the dimple may be on the order of magnitude of 0.03 inches. FIG. 24 includes a textured section 298 on container sleeve 296 to illustrate the concept of adding texture to a sleeve.

Other Vent Patterns.

This disclosure has shown two examples of vent systems with vents running down the sidewalls of the sleeves to allow air to flow from and to an area below the bottom of the slush bottle 440. In both instances, there were a set of four vents (212 and 1212) running down the sidewall of the sleeve (200 and 1200). The number of vents can be one or more and does not have to be four.

Likewise the pattern of vented space below the bottom of the slush bottle 440 may be any pattern that provides a path for air to move to and from the vents. The particular patterns shown in FIG. 7 and FIG. 20 are not required.

Container is a Flexible Bag.

FIG. 24 includes a slush container 480. Slush container 480 is a flexible container such as a bag. The slush container 480 may be filled with sterile saline at the point of manufacture or at the location seeking to use the surgical slush. An advantage of having the saline placed into the slush container 480 at the point of manufacture is that the staff at the location seeking to use the surgical slush would not need to seal the saline in the slush container 480 in a manner sufficient to withstand any mechanical agitation present in the slush making process. As there are a number of options for how slush is removed from the slush container 480, slush container 480 is shown without any particular feature used for removal of slush. A hybrid bag may have a wide mouth threaded opening that engages with a corresponding lid.

The slush container 480 may be partially filled with saline and contain air in addition to saline so that the slush making device may utilize the movement of the air within the slush container 480 as part of the process to agitate the slush as it forms. Alternatively the slush container 480 may be partially filled with saline and not contain air in addition to saline. In this latter case, the fact that the flexible bag is only partially filled may be useful as part of the process to agitate the slush as it forms as the shape of the flexible slush container 480 may change during stimulus to the sleeve assembly. In either case, the flexible slush container 480 may be said to be partially filled with saline as the flexible slush container 480 may receive additional saline. This flexing of the flexible slush container 480 will be reduced if the slush container 480 is filled to maximum capacity which may require a slush making device or process that is suitable for a maximally filled slush container 480.

FIG. 25 shows is a process 3000 for production of sterile surgical slush and delivery of the sterile surgical slush to a basin within a sterile field using a slush container that is a flexible container.

Step 3004—A flexible slush container 480 filled with sterile saline is placed within a sterile container sleeve. The slush container 480 and sterile container sleeve and sterile sleeve top are sized so that the slush container 480 may fit within the container sleeve or if the slush container 480 extends beyond the open end of the container sleeve, the slush container 480 is sized to be encapsulated by the combination of the container sleeve and an engaged sleeve top.

A developer may need to optimize the size of the flexible slush container 480 for a given sleeve assembly (or adjust a sleeve assembly for a given flexible slush container). The rate of cooling will be maximized if the sterile slush container 480 has lots of contact with the inner walls of the sleeve assembly. However, the slush making process may require some level of mechanical agitation of the sterile slush container 480 in order to avoid having a permanent layer of ice crystals on the inner wall of the sterile slush container 480. Thus, there may need to be some ability of the sterile slush container 480 to move relative to the sleeve assembly during the slush making process. Vents as described above may help with the insertion and removal of the slush container 480 from the container sleeve.

Step 3008—A sleeve top engages the open end of the container sleeve. Now the sterile saline material is contained within a sterile slush container 480 which is totally enveloped by a sterile sleeve assembly comprising a container sleeve and a sleeve top.

Step 3012—The sleeve assembly is placed within a slush making machine. The outside of the sleeve assembly is no longer sterile.

Note—the exterior of the sleeve assembly may be first deemed non-sterile when the sleeve assembly is placed into the slush making machine or may be deemed non-sterile before then. The exterior of the sleeve assembly could be deemed non-sterile even before the slush container is placed within the sleeve assembly as long as the interior of the sleeve assembly remains sterile.

Step 3016—After a period of time, the sterile saline is converted into sterile surgical slush. At least a portion of the sleeve or sleeve top is sufficiently translucent to allow the slush formed within the slush container 480 to be viewed. Alternatively, the process can work without observation through the sleeve or sleeve top and simply rely on the slush making cycle being sufficiently long to create slush.

Step 3020—Optional step—The sleeve assembly with sterile slush container 480 and sterile surgical slush may be held within the slush making machine at a maintain mode to maintain the sterile surgical slush until needed.

Step 3024—The sleeve assembly with the sterile slush container 480 and the sterile surgical slush is removed from the slush making machine and brought to the edge of the sterile field.

Step 3028—The sleeve top is removed by someone out of the sterile field to expose an end of the sterile slush container 480. Care is taken to avoid touching the slush container 480 as the slush container 480 is sterile and cannot be handled by someone outside of the sterile field. The sleeve top may be removed in a way consistent with the type of sleeve top. As previously discussed, it is optional, but advantageous, to have a sleeve top that is removed by a non-reversible process such as removal of the tear tab ring discussed above or some other seal with a tamper proof indicator that that allows a prior attempt to remove the sleeve top to be noticed.

The inclusion of a clear indication that the sleeve top has not been removed from the sleeve and then put back on the sleeve is particularly useful if the sterile slush container 480 encapsulated in the sleeve and sleeve top is at least temporarily out of view of the sterile field. This may happen where a large capacity slush making machine is placed close to several operating rooms.

Step 3032—A scrubbed staff member from the sterile field takes the sterile slush container 480 protruding from the non-sterile container sleeve without touching the non-sterile container sleeve that is held by a staff member outside of the sterile field. A slush container 480 that does not protrude from the open end of the container sleeve may be encouraged outward by placing the container sleeve substantially horizontally and squeezing near the bottom end of the container sleeve or providing other controlled stimulus while the container sleeve is substantially horizontal.

Step 3036—The scrubbed staff member can open the sterile slush container 480 immediately or later when additional sterile slush is needed. The exterior of the slush container 480 is still sterile and thus does not pose any complications for transfer of the sterile surgical slush within the sterile field. The slush container 480 may have any traditional type of opening included a large threaded cap at one end of the slush container or a destructive rip to open feature that allows for dispensing of the slush. Alternatively, the slush container 480 may be cut open.

Passing a sterile slush container 480 into the sterile field allows for a controlled delivery of sterile saline slush to the basin or other receptacle by a person within the sterile field. This minimizes the complications that might otherwise be present when a person outside of the sterile field attempts to pass sterile slush into the sterile field from a non-sterile container.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What is claimed is:

1. A method for production of sterile surgical slush outside of a sterile field and subsequent delivery of sterile surgical slush to the sterile field; the method comprising:
    placing a quantity of sterile saline into a non-sterile slush making device located outside of the sterile field, the sterile saline contained in a slush container, a set of interior and exterior surfaces of the slush container starting as sterile;
    the slush container enveloped by a sleeve assembly comprising a container sleeve that covers at least a portion of the slush container and a sleeve cap engaged with the container sleeve, the sleeve assembly is initially sterile but an exterior of the sleeve assembly is deemed not sterile not later than once the sleeve assembly with slush container is placed into the slush making device;
    removing the slush container enveloped by the sleeve assembly from the slush making device after conversion of the sterile saline to sterile surgical slush;
    separating the sleeve cap from the container sleeve to expose a portion of the slush container; and
    maintaining the slush container as sterile while removing the slush container from the container sleeve and moving the slush container into the sterile field so that the slush container may be opened and the sterile saline slush may be used when needed.

2. The method of claim 1 wherein separating the sleeve cap from the container sleeve to expose a portion of the slush container is achieved by separating the sleeve cap from the container sleeve to expose a lid and on a lid end of the slush container.

3. The method of claim 1 wherein separating the sleeve cap from the container sleeve to expose a portion of the slush container is achieved by separating the sleeve cap from the container sleeve to expose a bottom end of the slush container.

4. The method of claim 1 wherein the slush container comprises a flexible bag of saline.

5. The method of claim 1 further comprising providing sterile saline slush to a receptacle within the sterile field.

6. The method of claim 1 wherein the sleeve cap becomes engaged with the container sleeve and subsequent separating the sleeve cap from the container sleeve to expose the portion of the slush container requires destruction of a portion of the sleeve assembly so that the sleeve assembly is not accidentally used a second time.

7. The method of claim 6 wherein the destruction of the portion of the sleeve assembly requires destruction of a portion of the container sleeve.

8. The method of claim 6 wherein the destruction of the portion of the sleeve assembly requires destruction of a portion of the sleeve cap.

9. The method of claim 1 wherein the slush container comprises a slush bottle with a lid engaged with a lid end of the slush bottle.

10. The method of claim 9 wherein
    the sterile saline is poured into the slush bottle to partially fill the slush bottle;
    the lid is fastened to the slush bottle;
    the slush bottle is placed into the container sleeve; and
    the sleeve cap is placed over the slush bottle and engaged with the container sleeve before placing the sterile saline within the slush container within the sleeve assembly into the slush making device.

11. The method of claim 9 wherein
    the slush bottle is placed into the container sleeve;
    the sterile saline is poured into the slush bottle to partially fill the slush bottle;
    the lid is fastened to the slush bottle; and
    the sleeve cap is placed over the slush bottle and engaged with the container sleeve before placing the sterile saline within the slush container within the sleeve assembly into the slush making device.

12. The method of claim 1 wherein the container sleeve has a set of at least one longitudinal vent which allows air to move from a top end of the container sleeve to a space between an exterior bottom of the slush container and an interior bottom of the container sleeve to facilitate removal of the slush container from the container sleeve.

13. The method of claim 1 wherein insertion of the slush container into the container sleeve expands the container sleeve.

\* \* \* \* \*

UNITED STATES PATENT AND TRADEMARK OFFICE
CERTIFICATE OF CORRECTION

PATENT NO. : 9,561,895 B1  Page 1 of 1
APPLICATION NO. : 15/293612
DATED : February 7, 2017
INVENTOR(S) : Kammer et al.

It is certified that error appears in the above-identified patent and that said Letters Patent is hereby corrected as shown below:

In the Claims

Column 16, Line 24, 'and on a lid end' should read -and a lid end-.

Signed and Sealed this
Second Day of May, 2017

Michelle K. Lee
*Director of the United States Patent and Trademark Office*